US011045211B2

(12) United States Patent
Guastella

(10) Patent No.: US 11,045,211 B2
(45) Date of Patent: Jun. 29, 2021

(54) OSTEOTOMY SURGICAL INSTRUMENT

(71) Applicant: Claudio Guastella, Milan (IT)

(72) Inventor: Claudio Guastella, Milan (IT)

(*) Notice: Subject to any disclaimer, the term of this patent is extended or adjusted under 35 U.S.C. 154(b) by 49 days.

(21) Appl. No.: 16/559,651

(22) Filed: Sep. 4, 2019

(65) Prior Publication Data
US 2020/0121330 A1    Apr. 23, 2020

(30) Foreign Application Priority Data
Oct. 22, 2018   (IT) .................... 202018000003598

(51) Int. Cl.
*A61B 17/16*     (2006.01)
*A61B 17/17*     (2006.01)

(52) U.S. Cl.
CPC ...... *A61B 17/1688* (2013.01); *A61B 17/1732* (2013.01); *A61B 17/1785* (2016.11); *A61B 17/1606* (2013.01)

(58) Field of Classification Search
CPC .................. A61B 17/1606; A61B 17/1688
See application file for complete search history.

(56) References Cited

U.S. PATENT DOCUMENTS

| 4,385,628 A * | 5/1983 | Straith ............... A61B 17/1688 606/174 |
| 4,422,240 A * | 12/1983 | Wallace ............... A01G 3/0475 30/254 |
| 5,628,115 A * | 5/1997 | Hebert ..................... B25B 7/06 30/261 |
| 2005/0203556 A1* | 9/2005 | Olsen ..................... B26B 13/06 606/174 |
| 2019/0083108 A1* | 3/2019 | Dacosta ............ A61B 17/1606 |

FOREIGN PATENT DOCUMENTS

| DE | 29814344 U1 | 3/1999 | |
| DE | 102005004085 A1 * | 8/2006 | ......... A61B 18/1442 |

OTHER PUBLICATIONS

European Search Report; Munich; dated Feb. 14, 2020.

* cited by examiner

*Primary Examiner* — Nicholas W Woodall
(74) *Attorney, Agent, or Firm* — Patshegen IP LLC; Moshe Pinchas

(57) ABSTRACT

An attainment with an osteotomy surgical instrument for the nasal osteotomy is described; it is set up of at least a couple of lever arms and a couple of sharp spouts that are mutually hinged at least in a rotation fulcrum, where said sharp spouts show an active portion with the cross sectional having a sharp angle, in which the sharp angles of the two sharp spouts are opposed and said active portion extends for a length greater than 30 mm and shorter than 45 mm.

7 Claims, 3 Drawing Sheets

OSTEOTOMY SURGICAL INSTRUMENT

FIELD OF THE INVENTION

The invention herein refers to a surgical instrument, especially to an osteotomy surgical instrument.

RELATED ART

As it is known in the surgical field there are many manual instruments, specialised for single operations and usually long-established ones.

A particular field of surgical operations relates to osteotomies and specially to nasal osteotomies, namely those surgical operations in which nasal bones are involved, destined to carry out functional and/or aesthetical corrective operations.

In the rhinoplasty field, indeed, the term "osteotomies" is actually reserved to those—whole thickness or green wood—interruption movements—of bone sections, targeted to obtain an adequate remodelling of the bone structures of the nasal pyramid. Particularly the anatomic main situations, that the osteotomies are destined to correct are three:

closing of the open nasal septum deriving from the gibbotomy,
straightening of a deviated pyramid,
partial or total narrowing of a too wide bone pyramid.

To this aim, as a practice, it is necessary to carry out suitable fractures on the bone structures, with sharp instruments, in order to complete the manual operation, as soon as the osteotomic section is completed. The most commonly practised osteotomies are:

side osteotomies (both basal and intermediate)
transversal osteotomies
paramedian osteotomy (also called median).

The typically used manual instruments in these operations are chisel and saw, because the aim is to carry out long enough cuts in the delicate bone of the nasal area. To this end for side osteotomies the use of a sharp, straight or curved chisel, introduced intranasal has come out until now to be particularly effective (access carried out normally at the piriform opening) or from the outside.

Though the chisel produces an ideal bon cut type for this kind of osteotomies, it requires a remarkable expertise both for the correct routing of the same and for the beating force suitably applied on it by the surgeon require.

However, until now no valid alternatives have been found.

In the field of bone osteotomies in general, other types of surgical instruments are used, but they are not suitable for the use in nasal osteotomies. For example, rongeurs are known that are configured to cut the bones, but they are conceived to apply a high pressure in a localised position (with suitable formed jaws, like in the Luer forceps), so to cut strong big bones: therefore they are not suitable for the type of operation to be done in nasal osteotomies, where the cut must be precise, but with a certain extension.

BRIEF DESCRIPTION

Therefore, it is an aim of the invention, to propose a manual surgical instrument, that is particularly suitable to carry out nasal osteotomies, even without a remarkable expertise or dexterity.

Such aim is achieved with a surgical instrument for nasal osteotomy, set up of at least a couple of lever arms and a couple of sharp spouts mutually hinged at least in a rotation fulcrum, in which said sharp spouts show an active portion with cross section having an acute angle, in which the acute angles of the two sharp spouts are opposed and said active portion covers a length greater than 30 mm and shorter than 45 mm.

Other aspects of the invention according to the model are described in essential terms in the attached claims.

SHORT DESCRIPTION OF THE DRAWINGS

Further features and advantages of the invention will be anyway better apparent from the following detailed description, as a pure example and not limiting and it is explained in the attached drawings, in which:

FIG. 2A is a section view along the line A-A in FIG. 2, with a partial magnification enclosed in the dashed circle.

DETAILED DESCRIPTION OF AN ILLUSTRATIVE VERSION

Figures 1, 1A:
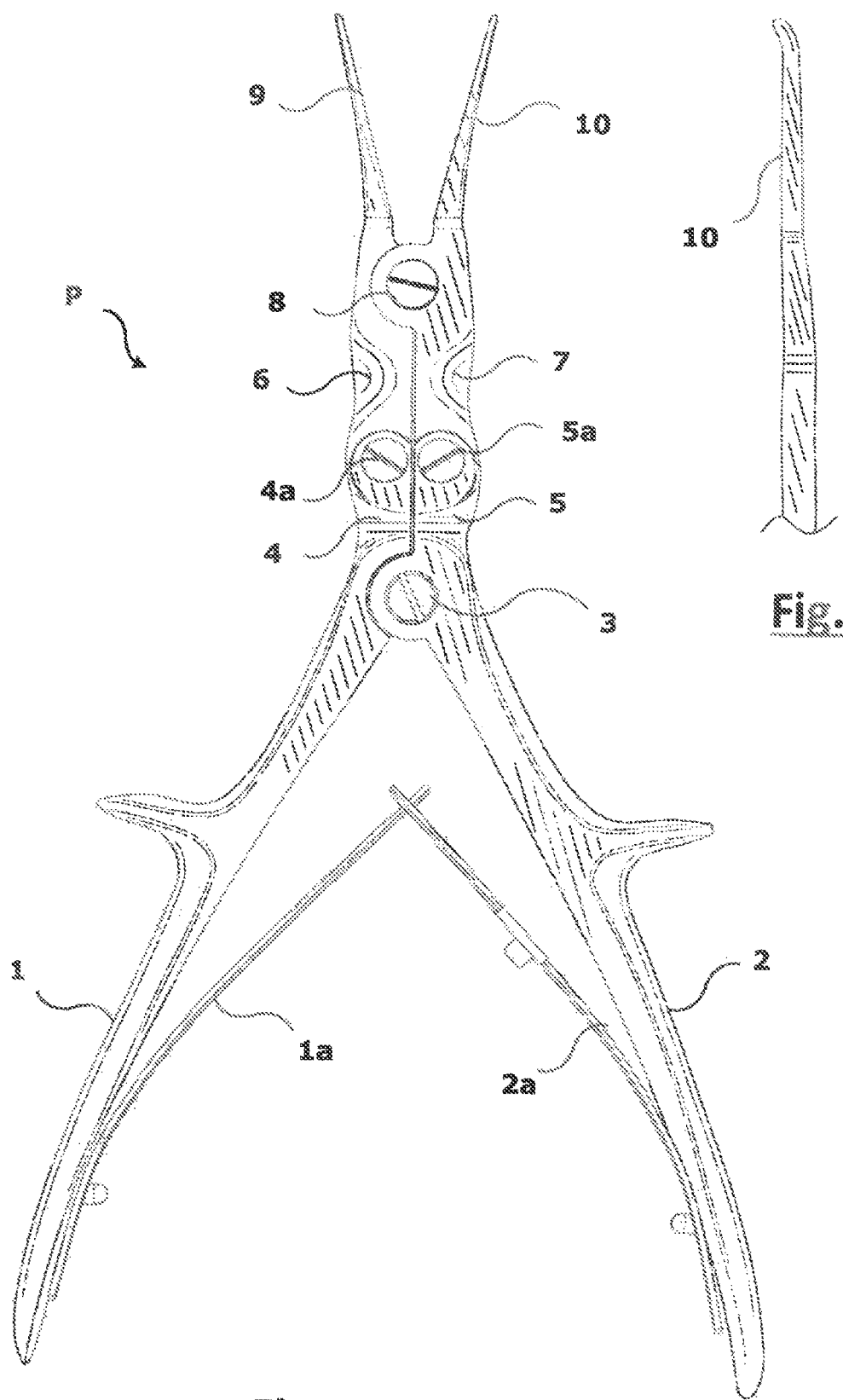
FIG. 1 is a front elevation view of a surgical instrument according to an illustrative version of the model, in an open position.
FIG. 1A is a side, interrupted, elevation view, of the cut apical part of the model.

In FIG. 1 a manual forceps P is shown composed of an illustrative known configuration. Two first lever arms 1 and 2 are mutually hinged as "a scissor" in a first fulcrum pin 3.

On the opposite side of the first fulcrum 3, the first lever arms 1 and 2 continue with short transmission spouts, 4 *e* 5 respectively, articulated in turn with related articulation pins 4a and 5a to a second couple of lever arms, 6 *e* 7 respectively, also mutually articulated as 'a scissor' in a second fulcrum pin 8.

On the opposite side of the second fulcrum 8, the second lever arms 6 and 7 continue with sharp spouts 9 and 10.

Figure 2:
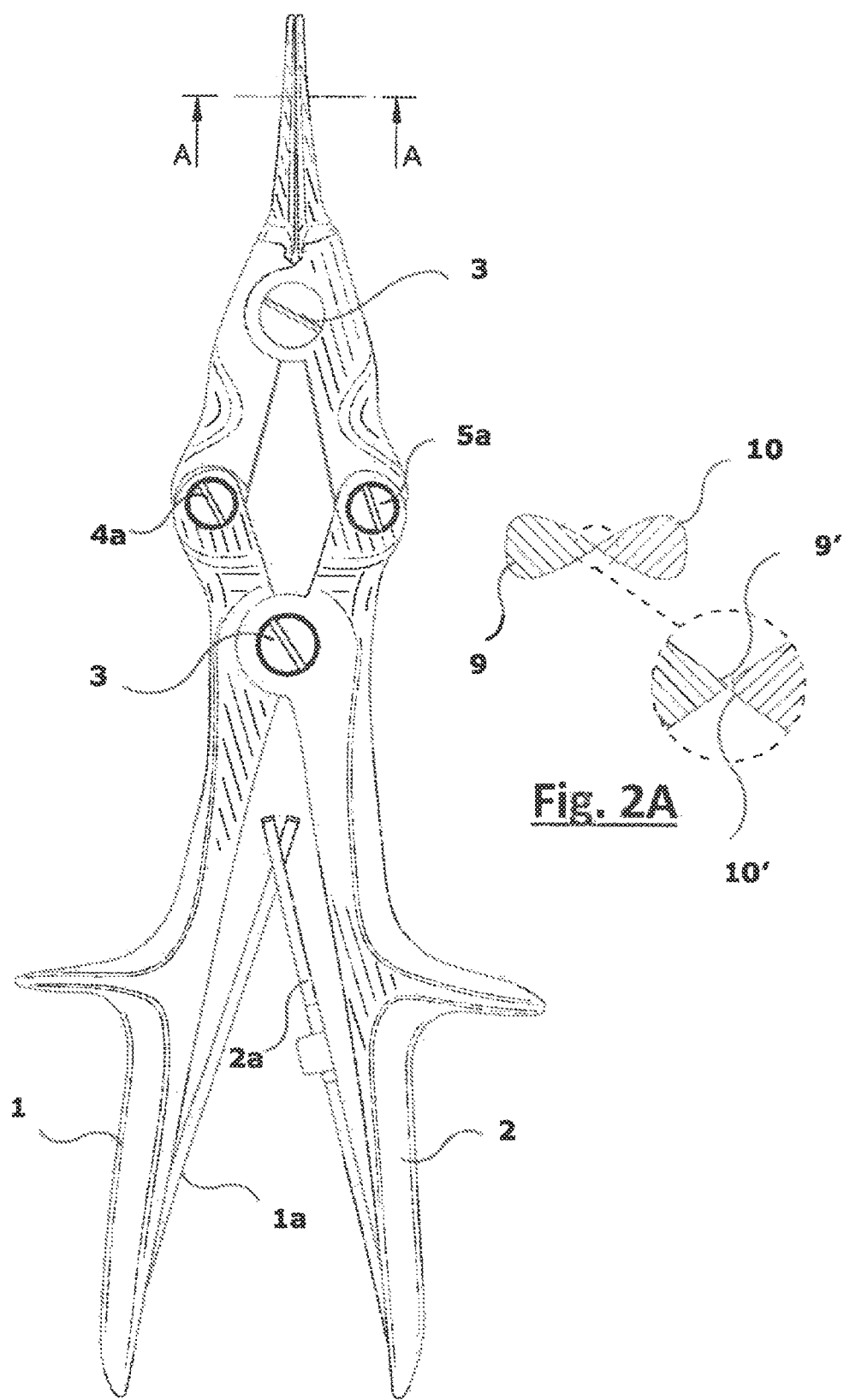
FIG. 2 is view like that of FIG. 1, with the instrument in a closed position.

Between the first two lever arms 1 and 2 preferably elastic back means are provided, for example harmonic reeds 1a and 2a, that stress the forceps in an open position, i.e. in a position in which the sharp spouts 9 and 10 are mutually retracted (as in FIG. 1). Intervening manually on the lever arms 1 and 2 to close the forceps and exercise the desired pressure action between the two sharp spouts 9 and 10 (FIG. 2), the harmonic reeds 1a and 2a are loaded to bring the forceps forward in the open position as soon as the manual action is released.

This forceps configuration is particularly effective to amplify the force applied on the lever arms 1 and 2 on the sharp spouts 9 and 10, but it does not exclude that even an alternative configuration may be used that supplies an analogous transmission effectiveness of the forces without providing two fulcra 3 and 8.

According to the model, each sharp spout 9 and 10 shows an active portion having an acute angle cross section (see figure FIG. 2A), as a typical blade, with the vertices of the acute angles of the two spouts that are mutually opposed.

Therefore, each one of the two sharp spouts 9 and 10 shows one sharp edge having an acute angle, preferably lower than 30°.

According to a preferred variation, one of the two sharp spouts 9 shows a sharp edge 9', while the other one 10 shows a corner 10', in which a groove having a triangular section is made being able to match up with the vertex of the opposed sharp edge (see the magnification of FIG. 2A). This configuration has proved to be particularly effective to carve as desired the nasal bone in the osteotomy operation.

As an alternative, the spouts 9 and 10 may provide blades that are composed of a double sharp blade on both sides.

For the specific nasal osteotomy, advantageously at least the active portion of the sharp spouts 9 and 10 extends for a length not shorter than 30 mm and not longer than 45 mm, preferably it is 35 mm. The width, in the elevation front view of FIG. 1, of each sharp spout 9 and 10 is as thin as possible, consistent with the material which it is built up of, in order not to be excessively intrusive in the introduction of the nose tissues, for example a width lower than 3 mm.

The blade of the acute angle corners extends on the active portion according to the straight line or according to a slightly curved line.

Preferably, the apical end of the sharp spouts 9 and 10 shows a slight curvature towards the front side, as it is well shown in the side view of FIG. 1A, for example a curvature that projects 3 mm approximately from the plane on which the blade of the main portion of the spouts 9 and 10 lies.

Figure 3:
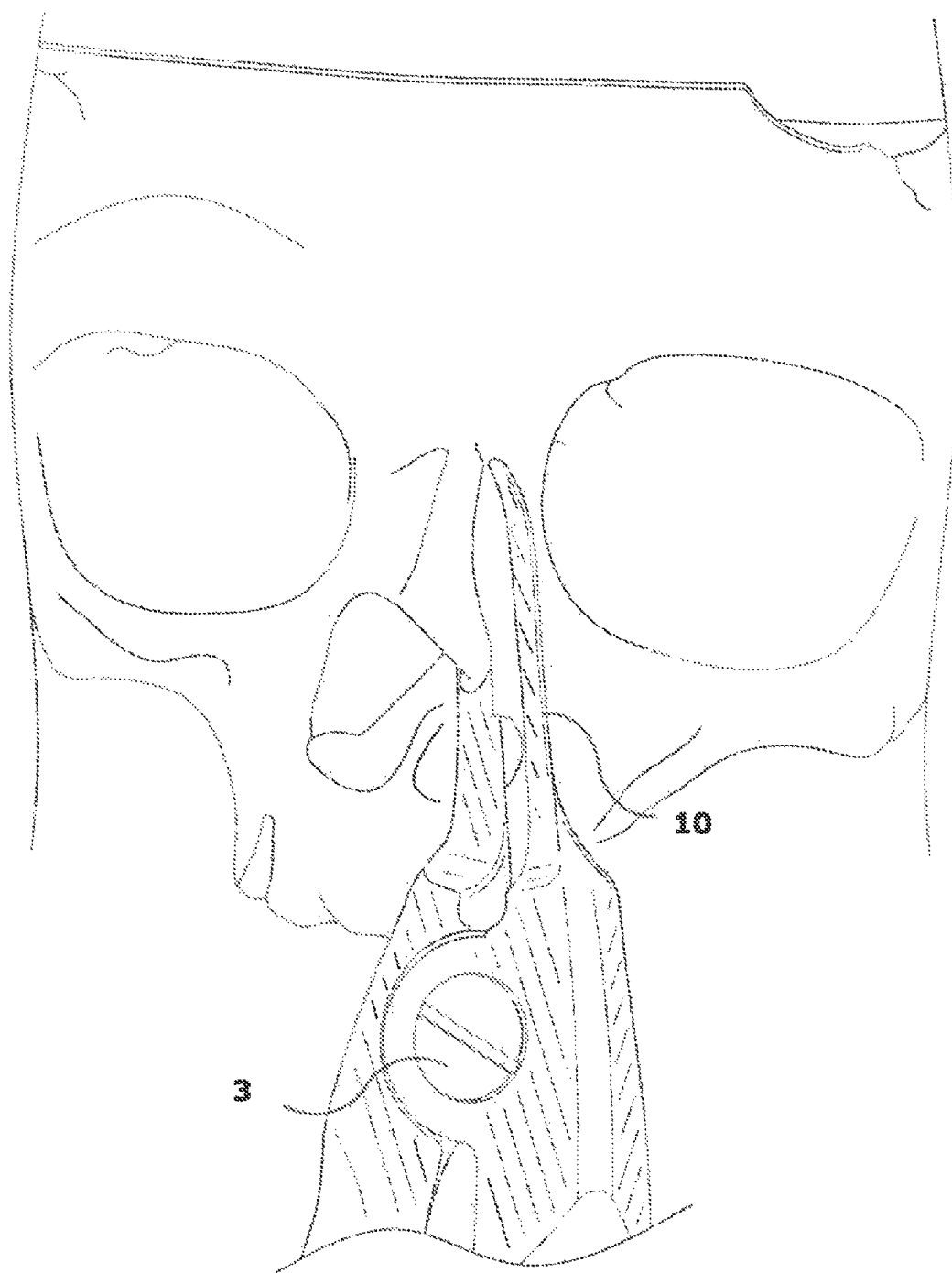
FIG. 3 is a schematic pictorial view, not to scale, showing the ways of use of the instrument according to the model.

With this configuration, the dimensions of the sharp spouts is sufficiently restrained to make their introduction in the desired site inside the nasal cavity possible, in both its side wall and in the side portion of the upright branch of the upper jaw near the nasal bone (see FIG. 3); at the same time, it is possible to carry out the nasal osteotomy with a short manual pressure intervention on the lever arms 1 and 2, without making the surgical instrument advance or without handling it, this makes the surgical operation easier, repeatable and quick.

As it is understood from the above-mentioned description, the surgical instrument according to the invention perfectly achieves the goals shown in the preliminary remarks. It is indeed possible to carry out nasal osteotomy operations in an easy and quick way, without using any chisel or saw, that need a remarkable expertise and operation dexterity.

The invention claimed is:

1. Surgical instrument for nasal osteotomy, comprising at least a couple of lever arms and a couple of sharp spouts mutually hinged at least in a rotation fulcrum, wherein said sharp spouts includes an active portion with cross sectional having acute angle, in which the acute angles of the two sharp spouts are opposed and said active portion extends for a length greater than 30 mm and shorter than 45 mm and wherein one of the said sharp spouts includes a sharp edge while the other of said sharp spouts includes a corner in which a groove having a triangular section is defined, said groove is configured to move with the vertex of the opposed sharp edge.

2. Surgical instrument of claim 1, wherein said active portion of the sharp spouts includes a cross width lower than 3 mm.

3. Surgical instrument of claim 1, wherein said active portion of the sharp spouts includes a sharp edge having an angle lower than 30°.

4. Surgical instrument of claim 3, wherein said blade edge extends on a straight line or on a slightly curved line.

5. Surgical instrument of claim 4, wherein an apical part of said sharp edge includes a curvature towards the front side of the instrument, that projects out of the plane of the remaining edge approximately by 3 mm.

6. Surgical instrument of claim 1, wherein said lever arms are hinged in a first fulcrum and they extend into transmission spouts, on their turn being articulated with related articulation pins to a second couple of articulated lever arms in a second fulcrum and that extends in said sharp spouts.

7. Surgical instrument of claim 1, wherein elastic stressing means between said lever arms are provided, that exercise a stretched elastic action to carve mutually said sharp spouts.

* * * * *